United States Patent [19]

Stroppolo et al.

[11] Patent Number: 5,500,226
[45] Date of Patent: Mar. 19, 1996

[54] PHARMACEUTICAL COMPOSITION HAVING ANALGESIC ACTIVITY

[75] Inventors: Federico Stroppolo, Pregassona, Switzerland; Daniele Bonadeo, Varese, Italy; Gian F. Fornasini, Milan, Italy; Annibale Gazzaniga, Rescaldina, Italy

[73] Assignee: Zambon Group S.p.A., Vicenza, Italy

[21] Appl. No.: 255,776

[22] Filed: Jun. 7, 1994

[30] Foreign Application Priority Data

Jun. 21, 1993 [IT] Italy .................................. MI93A1325

[51] Int. Cl.$^6$ .............................. A61K 9/14; A61K 9/20; A61K 31/19; A61K 31/195
[52] U.S. Cl. ...................... 424/466; 424/464; 424/465; 424/489; 514/557
[58] Field of Search .................................. 424/464, 465, 424/466, 489

[56] References Cited

U.S. PATENT DOCUMENTS 4,689,218  8/1987  Gazzaniga et al. ...................... 424/43
4,834,966  5/1989  Gazzaniga et al. ...................... 424/43

FOREIGN PATENT DOCUMENTS 0267321  5/1988  European Pat. Off. .
0424028  4/1991  European Pat. Off. .
89/00421  1/1989  WIPO .

OTHER PUBLICATIONS

Merck Index XI Ed., Library of Congress Catalog No. 89–600001, No. 4812, p. 776, 1989.

Drugs and the Pharmaceutical Sciences, Pharmacokinetics, Milo Gibaldi & Donald Perrier, pp. 293–296, Marcel Dekker Inc., New York, 1975.

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

A pharmaceutical composition for oral use having analgesic activity containing a mixture of arginine and (S)-Ibuprofen in a molar ratio between 1.1 and 1.9 is described.

6 Claims, No Drawings

PHARMACEUTICAL COMPOSITION HAVING ANALGESIC ACTIVITY

The present invention relates to a pharmaceutical composition with analgesic activity for oral use and, more particularly, it relates to a pharmaceutical composition for opal use containing S(+)-2-(4-isobutylphenyl)propionic acid and arginine.

2-(4-Isobutylphenyl)propionic acid, indicated hereinafter with the International Nonproprietary Name (INN) Ibuprofen, is a known non-steroidal anti-inflammatory drug (Merck Index XI ed., n. 4812, page 476) used in therapy for its analgesic, anti-pyretic and anti-inflammatory activity.

Notwithstanding Ibuprofen is used in therapy from years in racemic form, it is known, for some time, that its active enantiomer is the enantiomer with (S) configuration, hereinafter referred to as (S)-Ibuprofen.

It is also known that (S)-Ibuprofen has a more rapid, and consequently a more lasting, analgesic effect than Ibuprofen (International Patent Application WO 89/00421).

The need of pharmaceutical compositions able to anticipate the onset of the pharmacological effect of non-steroidal anti-inflammatory drugs is, in general, highly felt particularly in the analgesic therapy.

U.S. Pat. No. 4,689,218 (Zambon S.p.A.) describes Ibuprofen effervescent compositions containing 9–17% by weight Ibuprofen, 17–33% by weight arginine, 20–35% by weight sodium or potassium bicarbonate and 25–40% by weight sodium bitartrate which allow to obtain an increase of Ibuprofen maximum plasma concentration and a remarkable anticipation of the onset time of the analgesic effect.

U.S. Pat. No. 4,834,966 (Zambon S.p.A.) describes Ibuprofen water-soluble compositions containing 33–46% by weight Ibuprofen, 34–51% by weight L-arginine and 9–29% by weight sodium bicarbonate which allow to obtain an increase of Ibuprofen maximum plasma concentration and a remarkable anticipation of the onset time of the analgesic effect.

The molar ratio between arginine and Ibuprofen is between 1.1 and 1.5 while the weight ratio between sodium bicarbonate and Ibuprofen is between 0.25 and 0.75.

We have now found a pharmaceutical composition containing (S)-Ibuprofen and arginine able to significantly anticipate the onset of the analgesic effect after oral administration.

Therefore, object of the present invention is a pharmaceutical composition useful for the preparation of pharmaceutical forms for oral use consisting of a mixture of arginine and (S)-Ibuprofen in a molar Patio between 1.1 and 1.9.

(S)-Ibuprofen is used in the mixture in the form of free acid. Arginine is preferably L-arginine.

Preferably, the molar ratio between arginine and (S)-Ibuprofen is between 1.1 and 1.5.

Still more preferably, the molar ratio between arginine and (S)Ibuprofen is 1.1.

The composition object of the present invention allows to obtain a significant anticipation of the onset of the analgesic effect after oral administration and it is particularly useful for the preparation of pharmaceutical forms for oral use such as tablets, effervescent tablets, effervescent or hydrosoluble granulates, powders, syrups and solutions.

The preparation of the pharmaceutical compositions object of the present invention is carried out by mixing according to usual techniques.

For the formulation of the finished pharmaceutical forms, additional excipients suitable for the pharmaceutical use such as, for example, sweetening agents, flavouring agents, colouring agents, disintegrating agents, lubricants, diluents, anti-adhesion agents and absorbents can be added to the pharmaceutical composition object of the present invention.

Preferably, the pharmaceutical forms will contain an amount of (S)-Ibuprofen corresponding to 50 mg, 100 mg, 150 mg, 200 mg, 300 mg and 400 mg.

The preparation of the pharmaceutical forms is carried out according to conventional techniques of granulation, compression and dilution.

The peculiar characteristic of the composition object of the present invention is arginine.

In this regard, it is worth underlining that, differing from what is known for Ibuprofen in racemic form, the sole presence of an excess of arginine is able to produce a significant anticipation of the analgesic effect and a remarkable increase of the plasma concentrations (see Example 13).

In particular, it is not necessary the presence of other substances such as sodium or potassium bicarbonate.

As already underlined, the compositions object of the present invention allow to obtain a significant anticipation of the onset of the analgesic effect with respect to compositions containing only (S)-Ibuprofen.

An anticipation of the onset of the analgesic effect with the compositions object of the present invention results also in comparison with the onset of the analgesic effect of compositions containing an equivalent amount of (S)-Ibuprofen in the form of arginine salt (see Example 14).

From a practical point of view, this means that the analgesic effect begins before (generally after some minutes) and lasts longer.

It is not yet clear the mechanism according to which the compositions of the invention give rise to such a remarkable anticipation of the onset of the analgesic effect of (S)-Ibuprofen and to an increase of the plasma concentrations.

This result does not seem to be dependent on a partial or a total salification of (S)-Ibuprofen able to speed up the dissolution phase at gastric level.

In fact, the pharmacological effect of the composition according to the present invention is significantly higher than that of a composition containing an equivalent amount of active ingredient in the form of arginine salt (see Example 15).

Tentatively, a hypothesis of mechanism is that of an active role of free arginine in the phase of (S)-Ibuprofen absorption at gastric level.

Furthermore, this effect of arginine is still more surprising since the literature clearly shows that, in the case of racemic Ibuprofen, the action of arginine must be assisted by the contemporaneous presence of sodium bicarbonate or an equivalent thereof.

In order to better illustrate the present invention, the following examples ape now given.

Example 1

A mixture having the following composition

| (S)-Ibuprofen | 400 g |
| L-arginine | 371.6 g | was prepared by wet granulation and the granulate was dried in a static oven.

Example 2

A mixture having the following composition

| (S)-Ibuprofen | 400 g |
| L-arginine | 405.4 g | was prepared by wet granulation and the granulate was dried in a static oven.

Example 3

A mixture having the following composition

| | |
|---|---|
| (S)-Ibuprofen | 400 g |
| L-arginine | 439.2 g | was prepared by wet granulation and the granulate was dried in a static oven.

Example 4

A mixture having the following composition

| | |
|---|---|
| (S)-Ibuprofen | 400 g |
| L-arginine | 506.7 g | was prepared by wet granulation and the granulate was dried in a static oven.

Example 5

A mixture having the following composition

| | |
|---|---|
| (S)-Ibuprofen | 400 g |
| L-arginine | 641.8 g | was prepared by wet granulation and the granulate was dried in a static oven.

Example 6

Saccharose (1768.4 g), sodium saccharin (20 g), aspartame (60 g), apricot flavour (180 g) and sodium bicarbonate (200 g) were added to a mixture prepared as described in Example 1.

The resultant mixture was shared into about 1000 sachets having the following composition (3 g all):

| | |
|---|---|
| (S)-Ibuprofen | 400 mg |
| L-arginine | 371.6 mg |
| Saccharose | 1768.4 mg |
| Sodium saccharin | 20 mg |
| Aspartame | 60 mg |
| Apricot flavour | 180 mg |
| Sodium bicarbonate | 200 mg |

Alternatively, the mixture was homogenously shared into about 2000 sachets each weighing 1.5 g so containing an (S)-Ibuprofen amount corresponding to 200 mg.

Alternatively, the mixture was homogenously shared into about 4000 sachets each weighing 0.750 g so containing an (S)-Ibuprofen amount corresponding to 100 mg.

Example 7

Saccharose (1007.3 g), sodium saccharin (13.3 g), aspartame (40 g) and mint flavour (100 g) were added to a mixture prepared as described in Example 3.

The resultant mixture was shaped into about 666 paper-aluminum-polyethylene sachets having the following composition (3 g all):

| | |
|---|---|
| (S)-Ibuprofen | 600 mg |
| L-arginine | 658.8 mg |
| Saccharose | 1511.2 mg |
| Sodium saccharin | 20 mg |
| Aspartame | 60 mg |
| Mint flavour | 150 mg |

Alternatively, the mixture was shaped into sachets each weighing 1.5 g corresponding to 300 mg of (S)-Ibuprofen.

Example 8

Sorbitol (10074.4 g), sodium saccharin (80 g), aspartame (240 g) and raspberry flavour (800 g) were added to a mixture prepared as described in Example 2.

The resultant mixture was shared into about 8000 sachets having the following composition (1.5 g all):

| | |
|---|---|
| (S)-Ibuprofen | 50 mg |
| L-arginine | 50.7 mg |
| Sorbitol | 1259.3 mg |
| Sodium saccharin | 10 mg |
| Aspartame | 30 mg |
| Raspberry flavour | 100 mg |

Alternatively, the mixture was homogenously shared into about 4000 sachets each weighing 3 g so containing an (S)-Ibuprofen amount corresponding to 100 mg.

Example 9

Cross-linked polyvinylpyrrolidone (60 g), sodium bicarbonate (300 g) and magnesium stearate (4 g) were added to a mixture prepared as described in Example 1 and the whole was mixed up to homogeneity.

The mixture was compressed into about 1000 tablets having the following composition (1135.6 mg all):

| | |
|---|---|
| (S)-Ibuprofen | 400 mg |
| L-arginine | 371.6 mg |
| Cross-linked polyvinylpyrrolidone | 60 mg |
| Sodium bicarbonate | 300 mg |
| Magnesium stearate | 4 mg |

Alternatively, tablets weighing 567.8 mg or 283.9 mg each containing 200 mg or 100 mg of (S)-Ibuprofen respectively were prepared.

Example 10

A mixture, prepared as described in Example 1, was granulated with an aqueous solution of polyvinylpyrrolidone (10 g) and dried in a static oven.

Potassium bicarbonate (300 g), cross-linked polyvinylpyrrolidone (120 g) and magnesium stearate (8 g) were added to the resultant granulate and the whole was mixed up to homogeneity.

The mixture was compressed into about 2000 tablets having the following composition (604.8 mg all):

| | |
|---|---|
| (S)-Ibuprofen | 200 mg |
| L-arginine | 185.8 mg |
| Polyvinylpyrrolidone | 5 mg |
| Cross-linked polyvinylpyrrolidone | 60 mg |
| Potassium bicarbonate | 150 mg |
| Magnesium stearate | 4 mg |

Alternatively, about 4000 tablets weighing 302.4 mg or about 1000 tablets weighing 1209.6 mg each containing 100 mg or 400 mg of (S)-Ibuprofen respectively were prepared.

Example 11

Sodium bicarbonate (2400 g), sodium bitartrate (2414 g), aspartame (70 g), raspberry flavour (200 g) and gum-arabic (40 g) were added to a mixture prepared as described in Example 4.

The resultant mixture was compressed so obtaining about 2000 effervescent tablets (3015.3 mg) having the following composition:

| | |
|---|---|
| (S)-Ibuprofen | 200 mg |
| L-arginine | 253.3 mg |
| Sodium bicarbonate | 1200 mg |
| Sodium bitartrate | 1207 mg |
| Aspartame | 35 mg |
| Raspberry flavour | 100 mg |
| Gum-arabic | 20 mg |

Alternatively, about 4000 effervescent tablets weighing 1507.7 mg each containing 100 mg of (S)-Ibuprofen were prepared.

Example 12

Sodium bicarbonate (2400 g), sodium bitartrate (2414 g), aspartame (70 g), mint flavour (200 g) and gum-arabic (40 g) were added to a mixture prepared as described in Example 5.

The resultant mixture was compressed so obtaining about 2000 effervescent tablets (3082.9 mg) having the following composition:

| | |
|---|---|
| (S)-Ibuprofen | 200 mg |
| L-arginine | 320.9 mg |
| Sodium bicarbonate | 1200 mg |
| Sodium bitartrate | 1207 mg |
| Aspartame | 35 mg |
| Mint flavour | 100 mg |
| Gum-arabic | 20 mg |

Alternatively, about 4000 effervescent tablets weighing 1541.5 mg or about 8000 effervescent tablets weighing 770.7 mg each containing 100 mg or 50 mg of (S)-Ibuprofen respectively were prepared.

Example 13

An aqueous solution (100 ml) of a granulate prepared as described in Example 1 consisting of 400 mg of (S)-Ibuprofen and arginine (371.6 mg) (Preparation A) and an aqueous suspension (100 ml) containing 400 mg of (S)-Ibuprofen (Preparation B) were administered in a single dose to 8 subjects with mean age 37.6 years.

Each subject was apparently healthy particularly as far as the renal, hepatic and hematopoietic functions were concerned.

The experimental design consisted in randomized crossed administrations so that each subject received both preparations in two treatment sessions, with a wash out period of 7 days between the administrations.

The preparations were administered by oral route to subjects fasting since at least 8 hours.

At pre-established times: time zero (before treatment) and 5, 10, 15, 30, 45, 60, 90, 120, 240, 360 and 480 after the administration, about 7 ml of venous blood were withdrawn from each subject and put into test tubes containing heparin. Afterwards, plasma was prepared by centrifugation and kept at −20° C. until the analysis.

The analytical determination of (S)-Ibuprofen in the plasma samples was carried out by HPLC method with U.V. detector as described herein as follows.

Chromatographic conditions:

HPLC system (Jasco): pump 880-PU with detector 875-UV equipped with auto-sampler 851 AS Column: Chiral AGP, 100×4 mm, 5 μm (Chrom Tech) with a precolumn Chiral AGP 10×3 mm (Chrom Tech)

Mobile phase: (0.001M N,N-dimethyloctylamine 0.02M in sodium dihydrogen phosphate) 99% acetonitrile 1% pH 6.5 adjusted with NaOH 6M Flow: 1.2 ml/min Wavelength: 230 nm Propylparahydroxybenzoic acid was used as internal standard.

Procedure

HCl 3N (150 μl), a solution (50 μl) of internal standard (60 μg/ml of a mixture $CH_3CN$/phosphate buffer 0.01M pH 7.4) and phosphate buffer 0.01M pH 7.4 (31.25 μl) were added to plasma (250 μl). Cyclohexane (5 ml) was added, the mixture was stirred for 15 minutes and then centrifuged at 3500 rpm. An aliquot (3 ml) of the organic phase was drawn and the extraction was repeated with further cyclohexane (5 ml). The organic phases were collected and the solvent was evaporated under nitrogen flow. The residue was taken up with phosphate buffer 0.01M pH 7.4 (250 μl).

A sample (50 μl) was injected into the HPLC system.

Under the described operative conditions, the retention times (RT) were the following:

| | |
|---|---|
| (R)-Ibuprofen | RT = 3.5 min |
| (S)-Ibuprofen | RT = 4.8 min |
| Internal standard | RT = 10.2 min |

The obtained results are reported in table 1.

TABLE 1

Mean plasma concentrations of (S)-Ibuprofen (μg/ml) after oral administration of a composition of (S)-Ibuprofen, according to the present invention, containing 400 mg of (S)-Ibuprofen (Preparation A) and after oral administration of a composition containing (S) Ibuprofen (400 mg) (Preparation B).

| Time | Preparation A | Preparation B |
|---|---|---|
| 0 | 0 | 0 |
| 5 | 18.32 | 0.7 |
| 10 | 31.01 | 1.62 |
| 15 | 35.17 | 4.1 |
| 30 | 35.56 | 20.13 |
| 45 | 29.07 | 23.76 |
| 60 | 28.44 | 27.12 |
| 90 | 23.89 | 28.91 |
| 120 | 19.33 | 21.37 |
| 240 | 7.22 | 10.74 |
| 360 | 4.46 | 5.03 |
| 480 | 2.09 | 2.28 |

The following bioavailability parameters were calculated:

the area under curve of Ibuprofen concentration in plasma from t=0 to t=480 min ($AUC_{Obs}=AUC_{480}$) expressed as μg×min×ml$^{-1}$ was calculated according to the trapezoidal method (Gibaldi M. and Perrier D., Pharmacokinetics, pages 293–296, Marcel Dekker Inc. New York, 1975).

the area under curve of Ibuprofen concentration from t=0 to infinite ($AUC_{0\to\infty}$) was calculated by the following formula $$AUC_{0\to\infty}=AUC_{0\to 480}+AUC_{480\to\infty}$$

wherein $AUC_{480\to\infty}$=(S)-Ibuprofen plasma conc. after 480 min./$K_e$ and $K_e$=elimination constant the mean peak time ($t_{max}$) expressed as minutes was obtained by the average of the single peak times the mean peak concentration ($C_{max}$) expressed as μg/ml was calculated by the average of the single $C_{max}$ values.

the lag time (minutes) is the time between drug administration and the beginning of drug absorption.

The mean values of the above pharmacokinetic parameters are reported in table 2.

TABLE 2

Mean of the pharmacokinetic parameters of (S)-Ibuprofen calculated after oral administration of an (S)-Ibuprofen composition according to the present invention containing 400 mg of (S)-Ibuprofen (Preparation A) and after oral administration of an (S)-Ibuprofen composition (400 mg) (Preparation B).

| Parameters | Preparation A | Preparation B |
| --- | --- | --- |
| $t_{max}$ (min) | 28.15 | 73.03 |
| $C_{max}$ (μg/ml) | 38.82 | 29.41 |
| $AUC_{0\to 480}$ (μg · ml$^{-1}$ · min) | 6088 | 5913 |
| $AUC_{0\to\infty}$ (μg · ml$^{-1}$ · min) | 6537 | 6429 |
| Lag time (min) | 0.1 | 7.8 |

The obtained results show that the pharmaceutical compositions according to the present invention allow to obtain a remarkable anticipation of the absorption of the active ingredient (lag time) and, consequently, of the onset of the analgesic effect ($t_{max}$) and to reach plasma concentration levels significantly higher with respect to a composition containing the same amount of (S)-Ibuprofen ($C_{max}$).

Example 14

An aqueous solution (100 ml) of a granulate prepared as described in Example 1 containing 200 mg of (S)-Ibuprofen and arginine (Preparation C) and an aqueous solution (100 ml) containing an equivalent amount of (S)-Ibuprofen in the form of arginine salt (Preparation D) were administered in a single dose to 6 subjects.

Each subject was apparently healthy particularly as far as the renal, hepatic and hematopoietic functions were concerned.

The experimental design consisted in randomized crossed administrations so that each subject received both preparations in two treatment sessions, with a wash out period of 7 days between the administrations.

The preparations were administered by oral route to subjects fasting since at least 8 hours.

At pre-established times: time zero (before treatment) and 5, 10, 15, 30, 45, 60, 90, 120, 240, 360 and 480 after the administration, about 7 ml of venous blood were withdrawn from each subject and put into test tubes containing heparin.

Afterwards, plasma was prepared by centrifugation and kept at −20° C. until the analysis.

The analytical determination of (S)-Ibuprofen in the plasma samples was carried out by HPLC method with U.V. detector as described herein as follows.

Chromatographic conditions:

HPLC system (Jasco): pump 880-PU with detector 875-UV equipped with auto-sampler 851 AS Column: Chiral AGP, 100×4 mm, 5 μm (Chrom Tech) with a precolumn Chiral AGP 10×3 mm (Chrom Tech)

Mobile phase: (0.001M N,N-dimethyloctylamine 0.02M in sodium dihydrogen phosphate) 99% acetonitrile 1% pH 6.5 adjusted with NaOH 6M Flow: 1.2 ml/min Wavelength: 230 nm Propylparahydroxybenzoic acid was used as internal standard.

Procedure

HCl 3N (150 μl), a solution (50 μl) of internal standard (60 μg/ml of a mixture $CH_3CN$/phosphate buffer 0.01M pH 7.4) and phosphate buffer 0.01M pH 7.4 (31.25 μl) were added to plasma (250 μl).

Cyclohexane (5 ml) was added, the mixture was stirred for 15 minutes and then centrifuged at 3500 rpm. An aliquot (3 ml) of the organic phase was drawn and the extraction was repeated with further cyclohexane (5 ml). The organic phases were collected and the solvent was evaporated under nitrogen flow. The residue was taken up with phosphate buffer 0.01M pH 7.4 (250 μl).

A sample (50 μl) was injected into the HPLC system.

Under the described operative conditions, the retention times (RT) were the following:

(R)-Ibuprofen RT=3.5 min (S)-Ibuprofen RT=4.8 min

Internal standard RT=10.2 min

The obtained results are reported in table 3.

TABLE 3

Mean plasma concentrations of (S)-Ibuprofen (μg/ml) after oral administration of a composition of (S)-Ibuprofen, according to the present invention, containing 200 mg of (S)-Ibuprofen (Preparation C) and after oral administration of a composition containing an equivalent amount of (S)-Ibuprofen in the form of arginine salt (Preparation D).

| Time | Preparation C | Preparation D |
| --- | --- | --- |
| 0 | 0 | 0 |
| 5 | 9.88 | 8.71 |
| 10 | 17.40 | 14.80 |
| 15 | 22.00 | 21.60 |
| 30 | 21.10 | 23.20 |
| 45 | 18.90 | 19.10 |
| 60 | 16.70 | 14.30 |
| 90 | 14.80 | 11.70 |
| 120 | 11.00 | 10.90 |
| 240 | 5.81 | 4.31 |
| 360 | 2.34 | 2.00 |
| 480 | 1.69 | 1.09 |

The following bioavailability parameters were calculated: the area under curve of Ibuprofen concentration in plasma from t=0 to t=480 min ($AUC_{Obs}=AUC_{0\to 480}$) expressed as μg×min×ml$^{-1}$ was calculated according to the trapezoidal method (Gibaldi M. and Perrier D., Pharmacokinetics, pages 293–296, Marcel Dekker Inc. New York, 1975).

the area under curve of Ibuprofen concentration from t=0 to infinite ($AUC_{0\to\infty}$) was calculated by the following formula $$AUC_{0\to\infty} = AUC_{0\to 480} + AUC_{480\to\infty}$$

wherein
$AUC_{480\to\infty}$=(S)-Ibuprofen plasma conc. after 480 min./$K_e$
and $K_e$=elimination constant
the mean peak time ($t_{max}$) expressed as minutes was obtained by the average of the single peak times
the mean peak concentration ($C_{max}$) expressed as µg/ml was calculated by the average of the single $C_{max}$ values.

The mean values of the above pharmacokinetic parameters are reported in table 4.

TABLE 4

Mean of the pharmacokinetic parameters of (S)-Ibuprofen calculated after oral administration of an (S)-Ibuprofen composition according to the present invention containing 200 mg of (S)-Ibuprofen (Preparation C) and after oral administration of a composition containing an equivalent amount of (S)-Ibuprofen in the form of arginine salt (Preparation D).

| Parameters | Preparation C | Preparation D |
| --- | --- | --- |
| $t_{max}$ (min) | 15 | 30 |
| $C_{max}$ (µg/ml) | 22.0 | 23.2 |
| $AUC_{0\to 480}$ (µg · ml$^{-1}$ · min) | 3681 | 3281 |
| $AUC_{0\to\infty}$ (µg · ml$^{-1}$ · min) | 3969 | 3444 |

The obtained results show that the pharmaceutical compositions according to the present invention allow to obtain a remarkable anticipation of the onset of the analgesic effect ($t_{max}$).

Example 15

Anti-inflammatory activity

The anti-inflammatory activity of a composition prepared as described in Example 1 (Composition A) and of a composition containing an equivalent amount of (S)-Ibuprofen in the form of arginine salt (Composition R) was evaluated.

The carrageenin edema model in the rat was adopted.
The experimental design was as follows:
animal species: Sprague Dawley rat
number and sex of animals: 5, males
administration route: oral, by gavage after a 16 hours fasting period
frequence of administration: single treatment
dose: 5 mg/kg in terms of (S)-Ibuprofen
control: carboxymethylcellulose 0.5%

The experimental edema was induced by injecting 0.1 ml of a 2% carrageenin solution into the plantar aponeurosis of the rat paw. Composition A, Composition R and carboxymethylcellulose were administered the same time of the carrageenin injection.

Measurements of the paw volume were carried out immediately before the carrageenin injection and at 5, 10, 15, 30, 45, 60, 75 and 90 minutes afterwards.

The anti-inflammatory effect was estimated by evaluating the differential values of the paw volume obtained subtracting the basal values to the absolute values.

The obtained results are reported in table 5.

TABLE 5

Mean values of the paw volume (ml) in rats treated orally with a composition according to the present invention (Composition A), with a composition containing an equivalent amount of (S)-Ibuprofen in the form of arginine salt (Composition R) and with carboxymethyl-cellulose (control).
Administered dose of (S)-Ibuprofen: 5 mg/kg.

| Time | Paw volume (ml) | | |
| --- | --- | --- | --- |
| (minutes) | Composition A | Composition R | Control |
| 5 | 0.010 | 0.029 | 0.043 |
| 10 | 0.018 | 0.036 | 0.039 |
| 15 | 0.025 | 0.041 | 0.070 |
| 30 | 0.053 | 0.088 | 0.148 |
| 45 | 0.122 | 0.136 | 0.167 |
| 60 | 0.138 | 0.130 | 0.190 |
| 75 | 0.133 | 0.155 | 0.220 |
| 90 | 0.164 | 0.181 | 0.225 |

The above results show that Composition A as well as Composition R were able to reduce the paw volume. This anti-inflammatory effect resulted to be significantly more marked after administration of Composition A than after administration of Composition R, particularly at the observation timepoints between 5 and 30 minutes.

What we claim is:

1. A pharmaceutical composition useful for the preparation of pharmaceutical dosage forms for oral use consisting of a mixture of arginine and (S)-Ibuprofen in a molar ratio between 1.1 and 1.9.

2. A pharmaceutical composition according to claim 1 wherein the molar ratio between arginine and (S)-Ibuprofen is from 1.1 to 1.5.

3. A pharmaceutical composition according to claim 1 wherein the molar ratio between arginine and (S)-Ibuprofen is 1.1.

4. A pharmaceutical dosage form for oral use containing a pharmaceutical composition according to claim 1 in admixture with pharmaceutically acceptable excipients.

5. A pharmaceutical dosage form according to claim 4 containing for a single dose an amount of (S)-Ibuprofen corresponding to 50 mg, 100 mg, 150 mg, 200 mg, 300 mg or 400 mg.

6. A pharmaceutical dosage form according to claim 4 in the form of tablets, effervescent tablets, effervescent or hydrosoluble granulates, powders, syrups and solutions.

* * * * *